United States Patent [19]

Lewis

[11] 4,231,121
[45] Nov. 4, 1980

[54] METACARPAL-PHALANGEAL PROSTHESIS

[75] Inventor: Frank M. Lewis, Cordova, Tenn.

[73] Assignee: Wright Dow Corning, Arlington, Tenn.

[21] Appl. No.: 55,054

[22] Filed: Jul. 5, 1979

[51] Int. Cl.³ .............................................. A61F 1/24
[52] U.S. Cl. ..................................... 3/1.91; 128/92 C
[58] Field of Search ................................. 3/1.9–1.911; 128/92 C

[56] References Cited

U.S. PATENT DOCUMENTS

| 3,506,982 | 4/1970 | Steffee ..................................... 3/1.91 |
| 3,728,742 | 4/1973 | Averill et al. ........................... 3/1.911 |
| 3,991,425 | 11/1976 | Martin et al. ............................ 3/1.91 |
| 4,156,296 | 5/1979 | Johnson et al. .......................... 3/1.91 |
| 4,166,292 | 9/1979 | Bokros ...................................... 3/1.91 |
| 4,180,871 | 1/1980 | Hamas ...................................... 3/1.91 |

Primary Examiner—Ronald L. Frinks
Attorney, Agent, or Firm—Scrivener, Parker, Scrivener and Clarke

[57] ABSTRACT

The disclosure is of a two-part prosthesis which is particularly designed and intended for intramedullary implantation in substitution for the metacarpophalangeal (MP), phalangeal-interphalangeal (PIP) or distal-interphalangeal (DIP) joints.

1 Claim, 8 Drawing Figures

METACARPAL-PHALANGEAL PROSTHESIS

BACKGROUND OF THE INVENTION

Prostheses for intramedullary implantation in the bones of the metacarpophalangeal and proximal interphalangeal joints have taken a variety of forms, among these being onepiece elastic devices, such as those disclosed in the U.S. Pat. Nos. 3,462,765, 3,593,342 and 3,681,786, two-part hinged devices such as that disclosed in U.S. Pat No. 3,466,669, and ball and socket joint devices such as those disclosed in U.S. Pat. Nos. 3,506,982, 3,805,302 and 4,156,296 and British Pat. No. 1,304,837. All of these types of devices have inherent disadvantages; the elastic devices being subject to mechanical failure after only moderate use, while the hinge and ball and socket types exhibit lack of hyperextension and poor adduction.

It has therefore been the principal object of this invention to provide an implantable prosthesis which is particularly suitable for replacement of the metacarpophalangeal and interphalangeal joints and which will provide complete articulation including normal adduction and abduction, flexion and extension.

SUMMARY OF THE INVENTION

The endoprosthetic device provided by the invention has two integrally formed components each with a stem for intramedullary implantation in the metacarpal and proximal phalanx bones respectively. The implanted phalanx component has a proximal head having in its proximal surface a part-spherical concave surface. The implanted metacarpal component has a distal head the distal surface of which is a part-spherical convex surface having the same radius of curvature as the concave surface of the phalanx component. In plan, the stems of the implanted components are positioned in the center lines of their respective bones, and the proximal stem has dorsal dsplacement with respect to the centerline of the bone.

DESCRIPTION OF THE INVENTION

Figure 1:
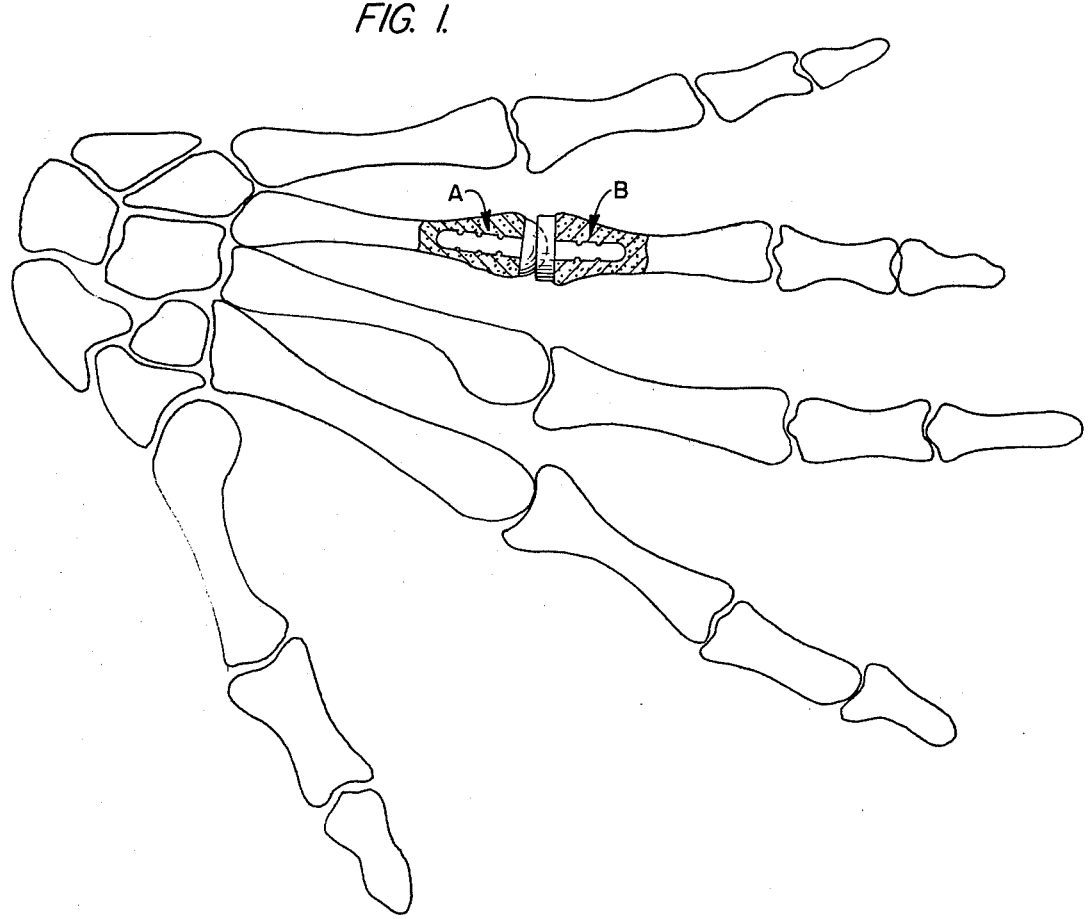
FIG. 1 is a plan view of the bone structure of the human hand showing the invention implanted to provide a substitute joint.
Figure 2:
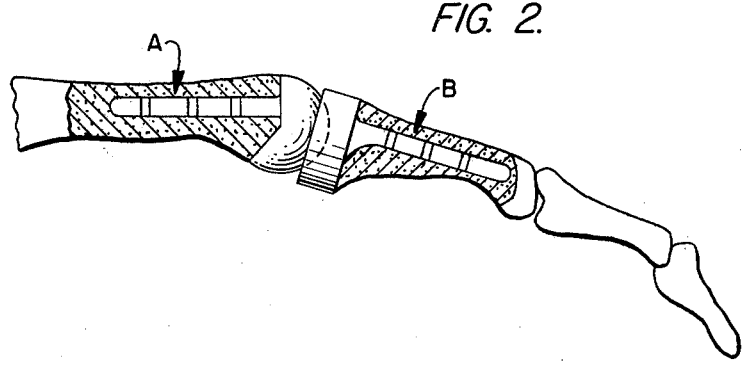
FIG. 2 is a side view of part of the hand of FIG. 1 showing the implanted prosthesis.

In the preferred embodiment of the invention, which is described and illustrated in this specification, the two components of the prosthesis are disclosed in FIGS. 1 and 2 as implanted in one of the metacarpal bones and the proximal phalangeal bone, but it will be understood that the prosthesis is also useful to provide a substitute for the interphalangeal and other joints of the human body, such as those of the toe.

The prosthesis comprises a metacarpal component A and a proximal phalanx component B both of which are constructed and intended for intramedullary implantation and which are provided with unconnected contacting surfaces providing a full range of natural joint motions.

Figure 3:
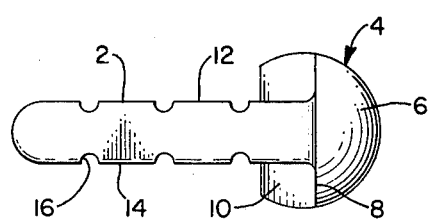
FIGS. 3, 4 and 5 are, respectively, plan, side and end views of the metacarpal component of the prosthesis.
Figure 4:
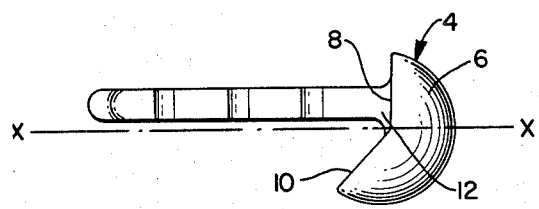
Figure 5:
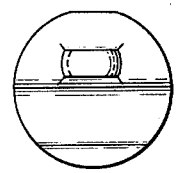

The metacarpal component A is a unitary body and, as particularly disclosed in FIGS. 3, 4 and 5, comprises, as implanted, a proximal stem 2 integrally connected to a distal head 4 which is provided with a smooth distal surface 6 of convex part-spherical configuration. In side elevation, as shown in FIG. 4, the part-spherical surface extends through an angle of approximately 225°, thus forming a proximal surface formed of intersecting flat surfaces 8 and 10 which intersect in a line 12 to form a dihedral angle. As shown in the side view of FIG. 4, the major axes of the surfaces 8, 10 are substantially equal. The stem 2, which is integral with the head, is connected to and extends at a right angle from the surface 8, and the surface 10 of the head therefore is inclined toward the stem at an angle of approximately 45°. Because of its connection to surface 8 of the head, and because of the relation between the surfaces 8 and 10, the stem 2 is displaced laterally of the plane X-X which passes through the apex line 12 of the dihedral angle formed by surfaces 8, 10, as shown in FIG. 4 while the longitudinal centerline of the stem lies in the plane which bisects the surface 8, as shown in FIG. 3.

Figure 6:
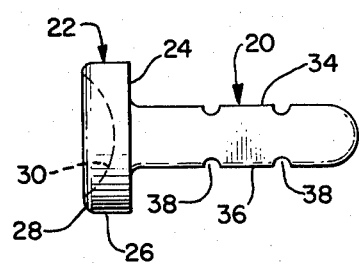
FIGS. 6, 7 and 8 are, respectively, plan, side and end views of the phalangeal component of the prosthesis.
Figure 7:
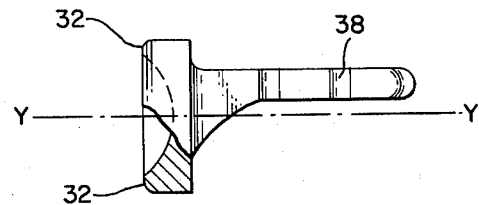
Figure 8:
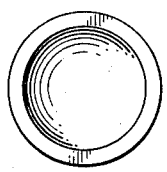

The phalanx component B is also a unitary body and, as particularly disclosed in FIGS. 6, 7 and 8, comprises as implanted a distal stem 20 integrally connected to a proximal head 22 which is defined by a circular distal surface 24 from which the stem 20 extends, a cylindrical peripheral surface 26 and a proximal circular surface 28 at least the major part of which is formed as a part-spherical concave smooth surface 30 having the same radius of curvature as the part-spherical convex surface 6 of head 4 of the metacarpal component. The concave surface is concentric with the peripheral surface 26, and in the disclosed embodiment is of less diameter than the head 22, leaving a radially curved convex surface 32 surrounding the concave surface 30.

The stem 20 is connected at a right angle to the distal surface 24 of the head 22 and is therefore parallel to the axis Y-Y of the head, and in accordance with the invention coincides with that axis is plan aspect, as shown in FIG. 6, and is laterally displaced with respect to that axis in side aspect, as shown in FIG. 7. As described above, the stem 2 of the metacarpal component is also parallel to and displaced laterally of the axis X-X of the head of that component, and the displacements of the stems in side aspect with respect to the center lines of the heads of the components of which they form parts are equal. In the implantation of the prosthesis this displacement of the stems of the two components causes the components to be positioned so that there is dorsal displacement of the stems, as shown in FIG. 2, thus increasing flexion and adduction of the joint, while the center lines of the stems of the two components coincide with the centerlines of the metacarpal bone and the proximal phalanx, as shown in FIG. 1.

The side edges of the stem of each component are provided with a plurality of transversely extending grooves 40 which are spaced along the length of the stem and provide, with the usual cement, additional fixation after intramedullary implantation.

The prosthesis will function successfully if made of any material suitable for human implantation, but it has been found that optimum results are produced by forming it of a graphite substrate coated with Pyrolytic carbon.

I claim:

1. An artificial joint for implantation into the living body to provide a total joint, consisting of:
   (a) a first component commmprising:
      i. a stem for intramedullary implantation into a bone,
      ii. a head formed integrally with the stem and transversely disposed thereto at one end thereof and being of cylindrical configuration with its axis parallel to the axis of the stem and laterally offset with respect thereto in one aspect and aligned therewith in an aspect turned 90°,
      iii. the outer surface of the head having a concentrically positioned concave depression therein of part-spherical shape, and
   (b) a second component comprising:
      i. a head formed integrally with a stem and being defined by:
      ii. a part-spherical convex outer surface and two flat surfaces which form a dihedral angle of 225°, and
      iii. a stem for intramedullary implantation into a bone formed integrally with the head and extending at right angles from one of the surfaces,
      iiii. the axis of the stem being within a plane bisecting the surface to which the stem is connected and being displaced laterally from a plane which includes the apex of the dihedral angle and is parallel to the stem,
   (c) the concave part-spherical surface of the first component and the convex part-spherical surface of the second component having the same radii and forming complementary articulating surfaces on implantation.

* * * * *